United States Patent [19]

Negersmith

[11] 4,002,269

[45] Jan. 11, 1977

[54] LIQUID PROPORTIONING SYSTEM IN A LIQUID SAMPLE ANALYZER

[75] Inventor: Kent M. Negersmith, Carmel, N.Y.

[73] Assignee: Technicon Instruments Corporation, Tarrytown, N.Y.

[22] Filed: Apr. 2, 1975

[21] Appl. No.: 564,583

Related U.S. Application Data

[63] Continuation-in-part of Ser. No. 498,015, Aug. 16, 1974, abandoned.

[52] U.S. Cl. .................................. 222/1; 23/230 R; 23/230 B; 23/253 R; 23/259; 222/145; 222/318

[51] Int. Cl.² .................. B67D 5/60; G01N 31/22; G01N 33/16

[58] Field of Search ......... 23/230 R, 230 B, 253 R, 23/259; 222/145, 1, 318; 137/255–262; 73/423 A

[56] References Cited

UNITED STATES PATENTS

| | | | |
|---|---|---|---|
| 2,953,155 | 9/1960 | Cummings | 137/256 |
| 2,995,425 | 8/1961 | Fuhrmann | 23/253 R |
| 3,028,225 | 4/1962 | Sheen | 23/253 R |
| 3,085,717 | 4/1963 | Anscherlik | 23/253 UX |
| 3,241,921 | 3/1966 | Ferrari | 23/253 R |
| 3,437,447 | 4/1969 | Harmon | 23/253 R |
| 3,572,130 | 3/1971 | Goldsmith | 23/259 X |
| 3,743,103 | 7/1973 | Isreeli | 23/253 R X |
| 3,831,618 | 8/1974 | Liston | 73/423 A X |
| 3,858,450 | 1/1975 | Jones | 73/423 A |

Primary Examiner—Norman Yudkoff
Assistant Examiner—Barry I. Hollander

[57] ABSTRACT

A liquid sample analyzer having a first fixed-volume chamber into which a first liquid is flowed filling it for subsequent displacement of the liquid volume therefrom by a second liquid into a substantially larger second fixed-volume chamber through a first port thereof, the second liquid acting as a pilot fluid. Prior to such liquid volume displacement from the first chamber, the second chamber, having an overflow outlet at a location remote with respect to the first port, is washed out and filled to an overflow level by a flow of the second liquid entering the second chamber through a second port. On such displacement of the volume of the first liquid into the second chamber, the last-mentioned volume and a relatively small volume of the second liquid entering the second chamber displace from the second chamber through the aforementioned outlet an equivalent volume of the second liquid, so that a reproducible volume of the first liquid remains in the second chamber with a reproducible volume of the second liquid. In this manner, the volumes of such liquids are precisely proportioned with substantial independence with respect to flow rates. One of the liquids may be a sample and the other may be a diluent. Sample analysis may take place in the second chamber prior to evacuation of the chamber contents therethrough the second port.

20 Claims, 4 Drawing Figures

LIQUID PROPORTIONING SYSTEM IN A LIQUID SAMPLE ANALYZER

This application is a continuation in-part of the applicant's copending application Ser. No. 498,015, filed Aug. 16, 1974 now abandoned.

BACKGROUND OF THE INVENTION

1. Field of the Invention

This invention relates to an automated liquid sample analyzer having a fluid system for proportioning two liquids in highly reproducible volumes, with substantial independence with respect to the flow rates of such liquids.

1. Prior Art

In automated apparatus for quantitatively analyzing sequentially a series of samples of blood or other liquids for one or more constituents of interest, it has been common to proportion various liquids utilized in the analytical process by employing a proportioning unit comprising a peristaltic pump and a manifold including compressible pump tubes. This general type of apparatus is illustrated, for example, in Skeggs et al U.S. Pat. No. 3,241,432 issued Mar. 22, 1966. Such liquid porportioning has been highly dependent on flow rates in the various manifold tubes. The flow rates and the liquid proportioning have been subject to variations effected by such factors as changes in the effective diameters of the tubes, temperatures and fluid viscosity for example. Changes in proportioning of liquids such as sample, diluent or reagent adversely affects the analytical results of such an automated analyzer.

It is also known that a shear valve has been utilized in an automated analyzer to provide a fixed-volume chamber for only a single liquid such as the sample to obtain a reproducible volume of such sample, the sample volume being displaced from the chamber toward an analysis station by a pilot fluid. One such apparatus is illustrated in Isrceli et al U.S. Pat. No. 3,583,232 issued June 8, 1971.

The present invention contemplates improved liquid proportioning in an automated analyzer.

SUMMARY OF THE INVENTION

An object of the invention is to provide in automated apparatus for a quantitative liquid sample analysis an improved system for proportioning plural liquids which are combined in the analysis process, which proportioning is substantially independent of flow rates.

Further, there is provided a liuqid sample analyzer having a first fixed-volume chamber into which a first liquid is flowed filling it for subsequent displacement of the liquid volume therefrom by a second liquid into a substantially larger second fixed-volume chamber through a first port thereof, the second liquid acting as a pilot fluid. Prior to such liquid volume displacement from the first chamber, the second chamber, having an overflow outlet at a location remote with respect to the first port, is washed out and filled to an overflow level by a flow of the second liquid entering the second chamber through a second port. On such displacement of the volume of the first liquid into the second chamber, the last-mentioned volume and a relatively small volume of the second liquid entering the second chamber displace from the second chamber through the aforementioned outlet an equivalent volume of the second liquid, so that a reproducible volume of the first liquid remains in the second chamber with a reproducible volume of the second liquid. One of the liquids may be a sample and the other may be a diluent. The contents of the second chamber may be analyzed therein and/or withdrawn for analysis elsewhere.

DETAILED DESCRIPTION OF THE INVENTION

Figure 1:
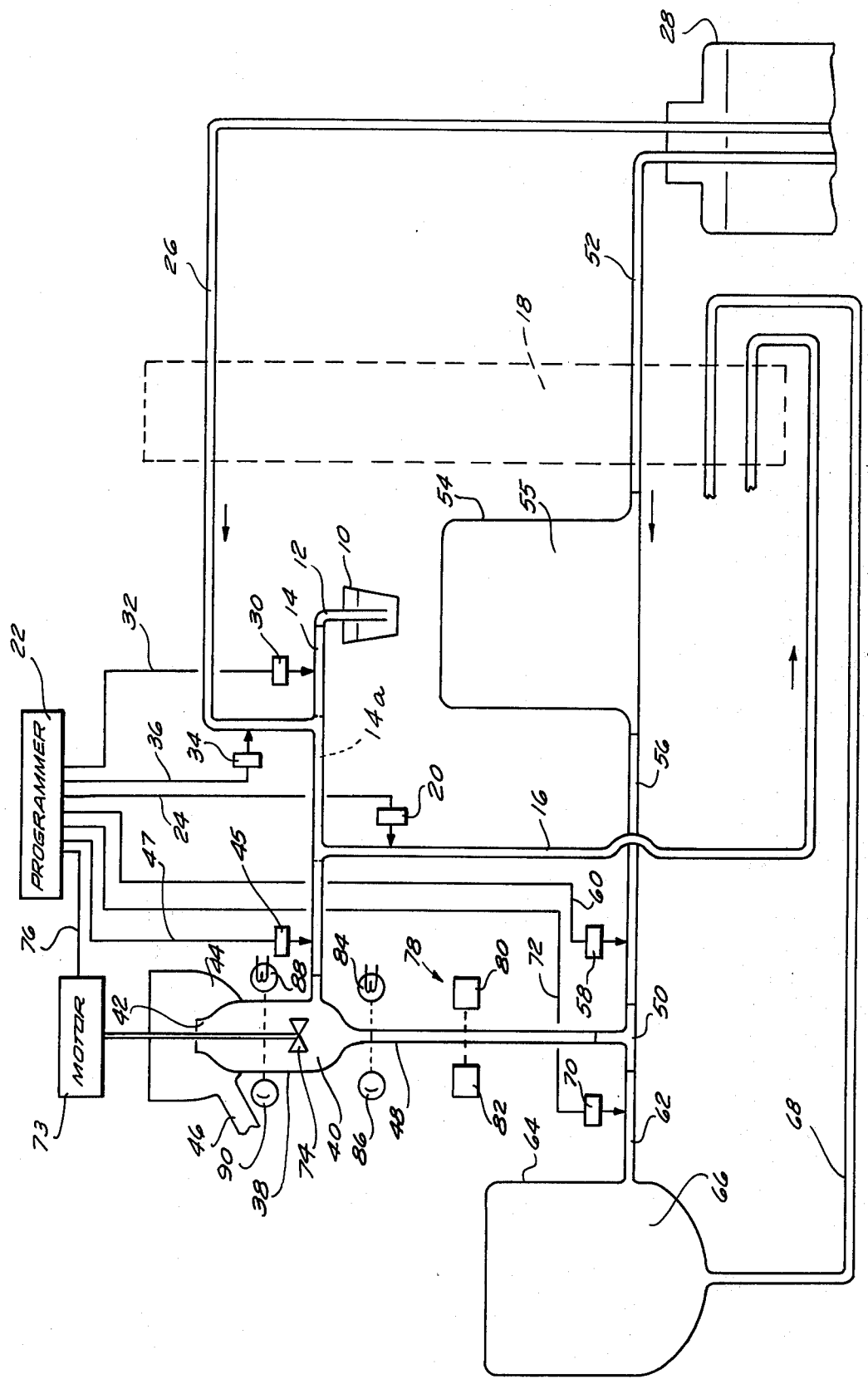
FIG. 1 illustrates diagramatically in a fragmentary view a liquid sample analyzer having a liquid proportioning system embodying the invention.

In the form of FIG. 1, there is provided a series of receptacles, each for containing sample liquid such as whole blood, for example, for quantitative analysis of plural constintuents therein such as hemoglobin and white cell count by way of example, one such receptacle being indicated at 10. An open-ended tubular probe 12 is shown immersed in the liquid of receptacle 10 and has an outlet end coupled to the inlet end of compressible tube 14. Connected to the tube 14 intermediate the ends thereof is the inlet end of a compressible tube 16 which extends through a peristaltic pump 18. In proximity to the junction of the tube 16 with the tube 14, there is a pinch valve 20 which is electrically operated and which cooperates with the compressible tube 16. A programmer 22 has an output to the input of a lead 24 which has an output to the valve 20. A compressible pump tube 26 has an inlet end immersed in the liquid of a container 28 which liquid is a diluent and may be Drabkin's reagent with a lysing agent. The tube 26 extends through the pump 18 and has an outlet connected to the tube 14 intermediate the end thereof connected to the probe 12 and the junction of the tube 14 with the tube 16. Intermedite the junction of the tube 14 with the tube 26 and the inlet end of tube 14, there is an electrically operated pinch valve 30 cooperating with the tube 14. The programmer 22 has an output which is connected to the input of lead 32 which has an output to the valve 30. Further, near the junction of the tube 26 with the tube 14, there is an electrically operated pinch valve 34 cooperating with the pump tube 26. The programmer 22 has an output to the input of a lead 36 having an output to the valve 34. The portion 14a of the conduit 14 between the junctions of the latter with the conduits 16 and 26 constitutes a first chamber, and the conduit 16 constitutes an overflow for the first chamber.

A body or flowcell 38 is provided defining a vertically arranged second chamber 40 having a restricted overflow outlet 42 in the top thereof and extending upwardly through the bottom of an integral bowl shaped catch basin 44, the basin being open to atmosphere at the top and having a lower lateral drain outlet 46 waste. The flowcell 38 has a lower lateral opening or first port to which the outlet of the compressible tube 14 is connected. A pinch valve 45 cooperates with the tube 14 near the outlet end thereof. The programmer 22 has an output to the input of a lead 47 which has an output to the valve 45. In the illustrated form, the body or flowcell 38 is structured of a transparent substance such as glass so that the contents of the body may be photometrically analyzed in the second chamber 40 in a manner which will be described hereinafter.

The flowcell 38 has an inlet-outlet bottom opening or second port to which is connected one end of a tube 48. In this form shown, the tube 48 is structured as a transparent glass flowcell for analysis of liquid in the tube 48 as will be described hereinafter. The other end of the tube 48 is connected to one arm of a T fitting 50.

A compressible tube 52 extends through the pump 18 and has an inlet end immersed in the diluent in the container 28. The outlet end of the tube 52 is coupled to a lower lateral inlet of a container 54 which has a lower lateral outlet coupled to the inlet end of a compressible tube 56. The outlet end of the tube 56 is connected to another arm of the T fitting 50. An electrically operated pinch valve 58 cooperates with the tube 56 in proximity to the T fitting 50. The programmer 22 has an output connected to the input of a lead 60 which has an output connected to the valve 58. The container 54 is closed except for the aforementioned connections thereof to the tubes 52 and 56, and forms a chamber 55 which in practice is preferably at least twice the size of the second chamber 40 defined by the flowcell 38. Air is constantly trapped in the chamber 55 above the diluent level therein and the aforementioned tube connections thereof. This trapped air serves to pressurize the chamber 55 when the valve 58 occludes the tube 56 and the chamber 55 is substantially filled with diluent by the action of the pump 18 on the pump tube 52. In the operation of the apparatus shown in FIG. 1, the pump 18 is operated continuously.

A compressible tube 62 has an inlet end connected to the remaining arm of the T fitting 50 and has an outlet end connected to a lateral inlet of a vessel 64 providing a chamber 66 which has a bottom outlet connected to the inlet end of a compressible tube 68 extending through the pump 18. Except for the aforementioned inlet and outlet connections, the chamber 66 is closed. In practice the chamber 66 is preferably at least twice the size of the second chamber 40. A pinch valve 70 cooperates with the tube 62 in proximity to the T fitting 50. The programmer 22 has an output to the input of a lead 72 which has an output to the valve 70. When the valve 70 occludes the tube 62, the action of the pump 18 on the pump tube 68 effects a vacuum in the chamber 66.

An electrical mixer motor 73 is suitably supported a distance above the catch basin 44. The motor shaft extends downwardly into the second chamber 40 through the overflow outlet 52 thereof, the shaft having a paddle 74 fast thereon. The programmer 22 has an output to the input of a lead 76 which has an output to the motor 73.

In this form, a particle counter, indicated generally at 78, is associated with a portion of the flowcell 48 and may take the form conveniently of the particle counter described in detail in Isreeli U.S. Pat. No. 3,511,573 issued May 12, 1970. The particle counter 78 includes a light source 80 from which a light path is directed through the flowcell onto a photomultiplier 82. The particle counter 78 is provided with non-illustrated data processing and analytical-result display as described in the lastmentioned patent. Operation of the particle counter 78 may be initiated in a conventional non-illustrated manner on opening of the valve 70. In this form, spaced upwardly from the particle counter 78 is a light souce 84 from which a light path is directed through the flowcell 48 onto a photocell 86. A signal from the photocell 86 may shutdown the operation of the particle counter in a conventional non-illustrated way and in a sequence to be described hereinafter.

As previously indicated, sample analysis may take place in the second chamber 40 of the flowcell 38, and this analysis may be a photometric analysis utilizing a colorimeter including a photocell operationally driving a pen recorder in the manner described in Skeggs U.S. Pat. No. 2,797,149 issued June 25, 1957. For present purposes, it is sufficient that for such analysis there is provided a light source 88 from which a light path is directed through the flowcell 38 and the second chamber 40 thereof onto a photocell 90.

In this form illustrated by way of example only, especially with reference to the particular sample and the tests performed thereon but not limited thereto the sample is whole blood and the analyses are for quantitative determinations of hemoglobin and white cell count.

The operation of the apparatus of FIG. 1 will now be described. It has been indicated previously that the sample receptacle 10 is one of a series of such receptacles, and for purposes of explaining the operation, the assumption is made that a sample of whole blood from another such receptacle, the first sample, has been previously aspirated into the apparatus, analyzed therein and discharged therefrom. When the probe 12 is immersed as shown in the sample of whole blood in the receptacle 10, the second sample, and valves 30 and 20 are the only valves in open condition, the second sample is aspirated through the probe 12 into the compressible tube 14 to fill the first chamber 14a with the overflow passing into the pump tube 16 through the action of pump 18. Concurrently, pump tue 52 aspirates diluent, in he form of the aforementioned Drabkin's reagent with a lysing agent, from the container 28 into chamber 55 causing the diluent therein to be pressurized. The mixer motor 22 is deenergized. As previously described, all the valves are controlled by the programmer 22. Valve 58 then opens allowing diluent to pass the valve in compressible tube 56, so that diluent from the pressure chamber 55 flows through the corresponding arms of fitting 50 and through the connected flowcell 48 and the flowcell 38 defining the second chamber 40 and out overflow outlet 42. This washes out traces of the first sample from the flowcell 48 and the fixed-volume second chamber 40 of the flowcell 38. The diluent exiting from the overflow outlet 42 spills into the catch basin 44 and leaves the latter through drainage outlet 46 thereof. Any gas present escapes through the outlet 42 to the atmosphere. A flow of the diluent from the pressure chamber 55 of 1.5 times the combined volumes of the second chamber 40 of the flowcell 38 and the flowcell 48 is presently considered the minimum volume necessary to washout and fill the second chamber 40 of the flowcell 38 and the flowcell 48. The valve 58 closes leaving these cells full of diluent. Concurrently with all the foregoing, the pump tube 68 through the action of the pump 18 effects a vacuum in the chamber 66 of the vessel 64.

Valves 30 and 20 closes and valves 34 and 45 open. This permits diluent from the container 28 to flow in pump tube 26 past the valve 34. This flow enters tube 14 and displaes the portion of the sample in the first chamber 14a formed by the tube 14 between the junction of tubes 14 and 26 and the junction of tubes 14 and 16. This sample portion is displaced past the valve 45 into the second chamber 40 of the flowcell 38 through the tube 14. It will be understood that the portion 14a of the tube 14 between the last-mentioned junctions thereof constitutes a fixed-volume liquid chamber. In such displacement of the fixed sample volume, this volume of the second sample displaces into the chamber 40 the relatively small volume of diluent in the tube 14 between the junction of the tubes 14 and 16 and the outlet of the tube 14, which diluent has remained in this tube portion from displcement in similar manner of the fixed volume of the preceding or first sample. In such displacement of the second sample volume into the second chamber 40, the diluent from the tube 26 serves as a pilot fluid, and a relatively small amount or volume of such pilot fluid follows the second sample volume into the second chamber 40 prior to simultaneous closing of the valves 34 and 45. The sample does not diffuse to any significant extent when entering the lower portion of the second chamber 40, and hence, the sample volume and such diluent entering the second chamber 40 with it displace through the chamber overflow outlet 42 an equivalent amount or volume of diluent only. In this manner, highly reproducible volumes of both sample and diluent are achieved with substantial independence with respect to flow rates. It will be understood from the foregoing that any desired fixed volume of sample may be chosen by selection of the length and/or the internal diameter of the portion 14a of the tube 14 between the junction of the tubes 14 and 16 and the junction of the tubes 14 and 26, which forms the first chamber. The last-mentioned tube portion may be rigid and formed of glass, if desired, for even greater reproducibility.

When the valves 34 and 45 are closed, the mixer motor 73 is energized by the programmer 22 with consequent mixing of the liquid contents of the flowcell 38. This mixing results in hemolysis of the erythrocytes of the sample in the flowcell 38. During the entry of the sample into the cell 38 and during hemolysis, the sample does not tend to diffuse into the flowcell 48 owing to the relatively very small inner diameter of the flowcell 48. Hemolysis in the flowcell 38 enables measurement of hemoglobin in the sample utilizing the aforementioned photocell 90. The mixer motor 73 is deenergized by the programmer 22.

The valve 70 then opens, which initiates operation of the particle counter 78, and the vacuum in the chamber 66 of the vessel 64 draws the liquid contents of the flowcell 38 through the flowcell 48 while the white cells or leukocytes of the sample are counted in the flowcell 48. The diluted sample, emptying first from the flowcell 38 and then the flowcell 48, flows through the corresponding arms of the T fitting 50 and through the tube 62 into the chamber 66. As the liquid level on the flowcell 48 falls below the light path on the photocell 86 the presence of air in the flowcell 48 is detected in a conventional manner by a decrease in light falling on the photocell 86 which generates a signal to shutdown operation of the particle counter 78. Liquids flowing into the chamber 66 is discharged therefrom by the action of the pump 18 on the pump tube 68. In this form, liquid conveyed by the pump tube 68 is discharged to waste as is the liquid conveyed by the pump tube 16. However, it will be apparent that a sample diluted in the second chamber 40 in the aforementioned manner may be withdrawn from the second chamber 40 through the pump tube 68 for subsequent treatment and analysis. It will be understood from the foregoing that when a diluted sample is discharged from the apparatus, the cycle may be repeated with a third sample of the series in a receptacle similar to the receptacle 10 and taking its place with reference to the probe 12.

It is to be understood that the form of the invention of FIG. 1 may be utilized for proportioning liquids other than sample and a diluent or reagent. For example, the invention may be utilized to proportion one unstable reagent with another reagent or to proportion one unstable diluent with another diluent. It will also be understood that the invention may be utilized for platelet and red cell counts of whole blood samples for example, and many chemistry tests on blood serum, urine and other liquids. It will also be apparent that the valves of the apparatus may be of a type other than pinch valves and may be associated with rigid tubing instead of compressible tubing In the form of FIG. 2, there is shown apparatus for proportioning liquids in a fluid sample analytical system, comprising an aspirating/dispensing probe, indicated generally at 98, structured of glass, for example. The probe 98 has a lower tube portion 100 with a lateral outlet 104 spaced upwardly from an inlet and outlet 102. The portion of probe 98 below the imaginary line 106, defines a second probe chamber, as will appear hereinafter. Above the line 106, a bulbous enlargement 108 communicates with portion 100 and also with an upper tube portion 110, which includes an inlet 112 and an outlet 114. The portion of the probe 98 extending between the imaginary line 106 to an imaginary line 116 defines a first probe chamber as will appear hereinafter.

The probe outlet 104 is coupled to the inlet of a compressible pump tube 118 which extends through a single-channel peristaltic pump 120 to waste. Inlet 112 is coupled to compressible pump tube 126, which extends through peristaltic pump 128 and has an inlet open to ambient air. Outlet 114 is coupled to compressible pump tube 132 which extends through a peristaltic pump 134 to waste. Pump tubes 118, 126 and 132 provide flow rates of 0.5 ml/min., 5.0 ml/min., and 5.0 ml/min., when the respective pumps 120, 128 and 134 are operated. A programmer 122 is connected along leads 124, 130 and 136 to selectively energize pumps 120, 128 and 134, respectively.

Figure 2:
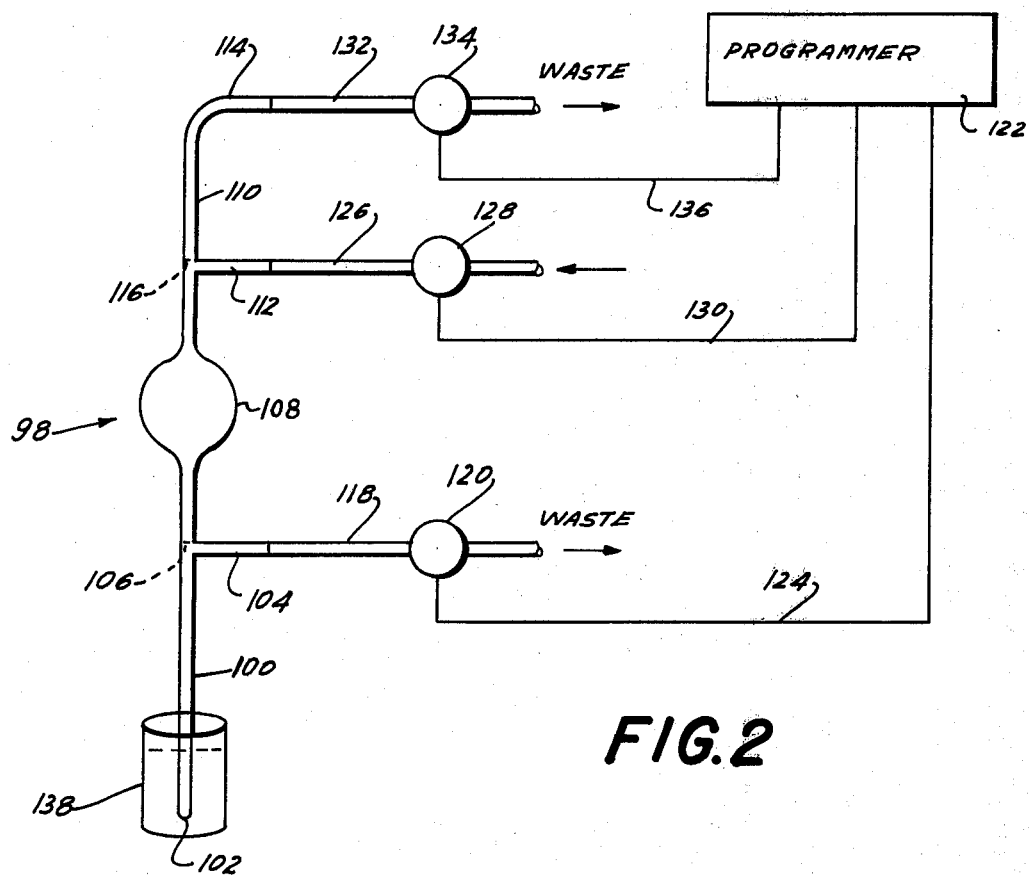
FIG. 2 is a diagramatic fragmentary view illustrating a modified form of the invention, showing a liquid porportioning probe immersed in a soruce of one liquid.

The operation of the form of the invention shown in FIGS. 1–4 will now be described. When probe 98 is immersed in a liquid receptacle 138, as shown in FIG. 2, programmer 122 energizes pump 120 to clear outlet 104 of any residual liquid. Subsequently, programmer 122 energizes pump 134, while pump 120 remains energized, which aspirates liquid from receptacle 138 to fill probe portions 100, 108 and 110, with excess liquid flowing to waste through the tubes 118 and 132, respectively. In this manner, probe portions 100, 108 and 110 are washed to remove any residue from the previous cycle of operation. Subsequently, pump 134 is deenergized by programmer 122 while the operation of the pump 120 is continued and probe 98 transferred from receptacle 138 and immersed in a liquid in receptacle 140, shown in FIG. 3. During this transfer, air is aspirated into probe 98 to further wash the second chamber below line 106, followed by the liquid from the receptacle 140. Such liquid fills the second chamber below line 106, any excess being outletted to waste along tube 118. In this condition, the first probe chamber between lines 106 and 116 remains filled with the previously aspirated liquid from receptacle 138.

The programmer 122 then deenergizes pump 120 and liquid flow in probe 98 ceases. The probe 98 is then transferred from the receptacle 140 to a dispensing position above receptacle 142. Receptacle 142 may be empty, as shown, or may contain one or more different liquids in predetermined volumes. The programmer 122 then energizes pump 128 which pumps gas or air along tube 126 and into probe inlet 112, which gas acts as a pilot fluid to eject the respective contents of the first and second chambers through probe outlet 102 and into receptacle 142. In so doing, liquid in the first chamber between lines 196 and 116 acts as a pilot fluid to displace liquid in the second probe chamber below line 106. Pump 128 is deenergized by programmer 122 to end the cycle of operation. The next cycle may then commence utilizing another set of receptacles such as the receptacles 138, 140 and 142 previously described.

It is obvious that the relative sizes of the first and second probe chambers may be varied according to the ratio of the first and second liquids to be mixed. Such liquids are many and diverse in character. For the purpose of illustration, the liquid from receptacle 138 may be a diluent, while the liquid from receptacle 140 may be a blood serum sample to be analyzed for a particular constituent. Also, an appropriate reagent or reagents for reaction with the sample may be contained in or added to receptacle 142 prior or subsequent to the dispensing operation. The reaction product in receptacle 142 may be measured by conventional techniques, e.g., photometry.

Figure 3:
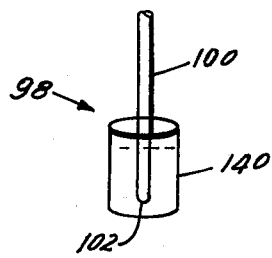
FIG. 3 is a fragmentary view illustrating the probe of FIG. 2 transferred relatively to the first liquid source and immersed in a source of a second liquid.
Figure 4:
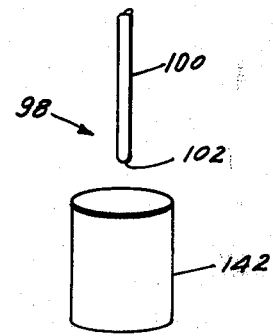
FIG. 4 is a fragmentary view illustrating the probe of FIG. 2 transferred realtively to the source of the second liquid and in a position to dispense the first and second liquids together into a receptacle in proportioned condition.

Transfer of the probe 98 between receptacles 138, 140 and 142, shown in FIGS. 2–4, and relative movement therebetween to effect the successive positioning of different sets of receptacles with respect to probe 98 may be accomplished by automated apparatus known in the art. Alternatively, the relative transfer of probe 98 may be by manipulation of the respective receptacles while the probe is stationary.

The form of the invention of FIGS. 2–4, like the form of FIG. 1 provides apparatus and a method for proportioning plural liquids in highly reproducible volumes, with substantial independence with respect to the flow rates of such liquids in liquid sample analysis. the invention includes the utilization of plural fixed-volume chambers each with an overflow outlet, and further includes the use of a pilot fluid to empty a liquid volume in at least one of such chambers.

While two forms of the invention have been illustrated in the drawings, it will be apparent, especially to those versed in the art, that the invention is susceptible of changes in details and may take other forms without departing from he principles of the invention.

What is claimed is:

1. A method of proportioning liquids in a fluid sample analyzer, comprising the steps of:
   filling a first chamber of fixed-volume with a first liquid;
   filling a second larger chamber of fixed-volume with a second liquid to be combined with said first liquid;
   displacing the volume of said first liquid in said first chamber into said filled second chamber, using a quantity of said second liquid as a pilot liquid; and
   exhausting concurrently a volume of said second liquid by overflow from said second chamber equal to said volume of said first liquid and any pilot fluid introduced into said second chamber.

2. A method as defined in claim 1, further including the step of agitating the combined liquids in said second chamber to mix them.

3. A method as defined in claim 1, further including establishing a vacuum in a third chamber, and withdrawing with such vacuum from said second chamber into said third chamber said combined first and second liquids.

4. A method as defined in claim 1, wherein: one of said liquids is a sample for analysis of a constituent thereof, and the other of said liquids is a reagent, and further including the step of analyzing the sample subsequent to the combining of said two liquids.

5. A method as defined in claim 1, wherein: said first liquid is a sample for analysis of a constituent thereof and said second liquid is a diluent, and further including washing out said second chamber with said second liquid from a pressurized source of the latter prior to said filling of said second chamber.

6. A method as defined in claim 1, wherein: said first liquid is a sample for analysis of a constituent thereof and said second liquid is a reagent, and further including the steps of subsequently withdrawing said combined liquids from said second chamber and analyzing the sample.

7. A method as defined in claim 4, wherein: said sample is whole blood and said reagent is Drabkin's reagent with a lysing agent, and further including the step of agitating the combined liquids in said second chamber to mix them for hemolysis of the erythrocytes of said sample, said second chamber comprising a flowcell, and said analysis being a photometric analysis of the said sample in said flowcell for hemoglobin in said sample.

8. A method as defined in claim 7, further including subsequently displacing the contents of the second chamber for flow thereof through a second flowcell, said analysis including a photometric analysis in said second flowcell for counting the leukocytes in said sample.

9. A method of proportioning liquids in a fluid sample analyzer utilizing a first fixed-volume chamber, a larger second fixed-volume chamber having an overflow outlet, and a controlled fluid coupling between said chambers for placing the latter alternatively in and out of communication with each other, comprising:
   filling said first chamber by flowing a first liquid along a conduit having an outlet coupled to said first chamber, while said chambers are out of communication;
   filling said second chamber by flowing a second liquid along a conduit having an outlet coupled to said second chamber, while said chambers are out of communication;
   flowing as a pilot fluid said second liquid along a conduit having an outlet coupled to said first chamber, while said chambers are in communication;
   displacing with said flowing second liquid from the lastmentioned conduit outlet the volume of said first liquid in said first chamber into said filled second chamber for displacement and overflow of an equivalent volume of said second liquid through said overflow outlet, and thereafter placing said chambers out of communication with one another; and withdrawing the combined volumes of said first and second liquids from said second chamber by flowing said combined liquids along a conduit having an end coupled to said second chamber, while said chambers are out of communication.

10. A liquid porportioning system in a fluid sampler analyzer, comprising:
  means for flowing a first liquid along a first conduit for filling means defining a first chamber of fixed volume;
  means for flowing a second liquid along a second conduit for filling means defining a second larger chamber of fixed volume;
  means for flowing a different quantity of said second liquid as a pilot fluid along a third conduit to said first chamber; and
  first means for selectively coupling said first chamber to said second chamber, the last-named means coupling said chambers during said flow of said pilot fluid, such that the volume of said first liquid in said first chamber is displaced into said filled second chamber, said means defining said second chamber comprising means for overflowing a volume of said second liquid from said second chamber equal to the volume of said first liquid and any pilot fluid introduced into said second chamber.

11. Apparatus as defined in claim 10, further including means for agitating the combined liquids in said second chamber to mix them.

12. Apparatus as defined in claim 10, further including means for terminating said flow of said second liquid along said second conduit toward said second chamber, means defining a third chamber, second means selectively coupling said second conduit to said third chamber, and means establishing a vacuum in said third chamber when said second coupling means is closed, the vacuum in said third chamber withdrawing into said third chamber the combined liquids in said second chamber through said second conduit when said second coupling means is open and said first coupling means is closed and said flow of said second liquid in said second conduit toward said second chamber is terminated.

13. Apparatus as defined in claim 10, wherein: one of said liquids is sample for analysis of a constituent thereof, and the other of said liquids is a reagent, and further including means for analyzing the sample subsequent to the combining of said two liquids.

14. Apparatus as defined in claim 10, wherein: said first liquid is a sample for analysis of a constituent thereof and said second liquid is a diluent, and further inlcuding a controlled pressurized source of said diluent coupled to said second conduit, said means for flowing said second liquid along said second conduit being operative to wash out said second chamber prior to said filling of said second chamber.

15. Apparatus as defined in claim 10, wherein: said first liquid is a sample for analysis of a constituent thereof and said second liquid is a reagent, and further including means terminating the flow of said second liquid in said second conduit toward the second chamber, means withdrawing said combined liquids from sad second chamber flow thereof along said second conduit when the flow of said second liquid therein toward the second chamber is terminated, and means for analyzing the sample in said second conduit.

16. In a liquid proportioning system in a fluid sample analyzer, having means defining a first fixed-volume chamber, means defining a larger second fixed-volume chamber having an overflow outlet, and a controlled fluid coupling between said chambers for placing the latter alternately in and out of communication with each oter, the combination of;
  means flowing a first liquid along a conduit having an outlet coupled to said first chamber for filling the latter, while said chambers are out of communication,
  conduit means comprising at least one liquid conduit having an end coupled to said second chamber;
  means flowing a second liquid along said conduit means for filling said second chamber, while said chambers are out of communication;
  means flowing said second liquid along a conduit having an outlet coupled to said first chamber to displace the volume of the first liquid in the latter into said filled second chamber, while said chambers are in communication, for displacement and overflow of an equivalent volume of said second liquid through said overflow outlet prior to said chambers being placed out of communication; and
  means coupled to said conduit means for withdrawing the combined volumes of said first and second liquids in said second chamber, while said chambers are out of communication.

17. Apparatus for proportioning liquids in a liquid sample analytical system, comprising: a conduit system including means defining a first and a second fixed-volume chamber in fixed relation to one another each having an inlet and an overflow outlet, means for filling said first chamber with a first liquid and said second chamber with a second liquid of different composition, through the respective inlets to overflow the respective outlets, and means for displacing said first liquid from said first chamber through said second chamber for dispensing from said conduit system through said second chamber inlet in combined form the volumes of said first and second liquids from said chambers, said means defining said chambers and said inlets and outlets thereof comprising a probe including a vertically arranged conduit having a lower opening for ingress and egress of said liquids which forms said inlet of said second chamber, said conduit having intermediate of its ends a lateral outlet forming said second chamber overflow outlet, said second chamber being formed by the portion of said conduit extending between said second chamber inlet and said second chamber overflow outlet, said conduit having a lateral fluid inlet spaced upwardly from the last-mentioned outlet, said first chamber being formed by the portion of the conduit extending between said second chamber overflow outlet and said lateral fluid inlet, said first chamber inlet being in direct communication with said second chamber, and said conduit having an outlet above said lateral fluid inlet and forming said first chamber overflow outlet.

18. Apparatus as defined in claim 17, wherein: said first and second chambers have different volumes.

19. Apparatus as defined in claim 17, wherein: said means filling said first and second chambers comprises means establishing at least a partial vacuum connected to the respective outlets of said first and second chambers.

20. Apparatus as defined in claim 17, wherein: said means for dispensing said liquid volumes comprises means flowing a pilot fluid through said first and second chambers.

* * * * *